United States Patent
Merrill

(10) Patent No.: US 7,211,066 B1
(45) Date of Patent: May 1, 2007

(54) ACTIVE SURFACE EXCHANGE CATHETER AND METHOD

(75) Inventor: Thomas L. Merrill, Windsor, NJ (US)

(73) Assignee: Focal Cool, LLC, East Windsor, NJ (US)

( * ) Notice: Subject to any disclaimer, the term of this patent is extended or adjusted under 35 U.S.C. 154(b) by 182 days.

(21) Appl. No.: 10/620,212

(22) Filed: Jul. 15, 2003

Related U.S. Application Data

(60) Provisional application No. 60/395,842, filed on Jul. 15, 2002.

(51) Int. Cl.
*A61F 7/12* (2006.01)
(52) U.S. Cl. .................................... 604/113
(58) Field of Classification Search ............ 604/96.01, 604/97.01, 97.02, 98.01, 99.01, 99.02, 100.03, 604/101.01, 103.01, 103.02, 113, 915, 916, 604/919, 920, 921; 606/191–194
See application file for complete search history.

(56) References Cited

U.S. PATENT DOCUMENTS

| | | | |
|---|---|---|---|
| 5,269,758 A * | 12/1993 | Taheri ..................... | 604/96.01 |
| 5,624,392 A * | 4/1997 | Saab .......................... | 604/43 |
| 5,885,244 A * | 3/1999 | Leone et al. ............... | 604/508 |
| 6,096,068 A * | 8/2000 | Dobak et al. .............. | 607/105 |
| 6,241,706 B1 * | 6/2001 | Leschinsky et al. ...... | 604/99.01 |
| 6,299,599 B1 * | 10/2001 | Pham et al. ................ | 604/113 |

OTHER PUBLICATIONS

William R. Milnor, Cardiovascular Physiology, Oxford University Press, New York, NY, 1990, p. 395.
Ralph L. Webb, Principles of Enhanced Heat Transfer, John Wiley & Sons, Inc., New York, NY, 1994, p. 2.
*IBID*, p. 50.
Milnor, p. 397.
G. L. Rockswold et al., Results of a Prospective Randomized Trial for Treatment of Severly Brain-Injured Patients with Hyperbarle Oxygen, Journal of Neurosurgery, vol. 76, 1992 pp. 929-934, Abstract Only.

* cited by examiner

*Primary Examiner*—Manuel Mendez
(74) *Attorney, Agent, or Firm*—Cooley Godward Kronish LLP

(57) ABSTRACT

Catheters for treating body fluids, particularly blood, include one or more tubes through which a working fluid is circulated. The fluid characteristics, e.g., temperature or drug content, interact with the body fluid by transfer through the tube walls. For enhancing the efficiency of such transfer, energy is added to the body fluid where it contacts the tube outer surfaces for reducing the thickness of thermal and concentration boundary layers at the tube surfaces. The energy adding is accomplished by causing pulsations in the walls of the tubes, or in the dimensions of a balloon parallel to the tubes, by means of pressure pulsations in the fluids circulated through the tubes and/or the balloon. Systems are disclosed for providing and controlling the circulation of various fluids and drugs through the catheter.

30 Claims, 15 Drawing Sheets common carotid artery

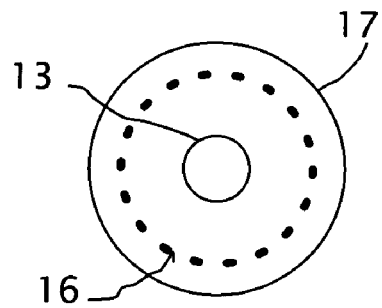
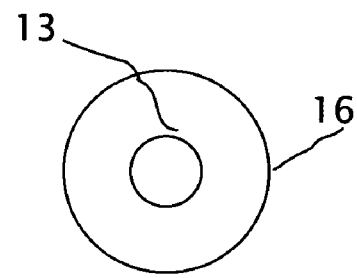
FIG. 12A          FIG. 12B
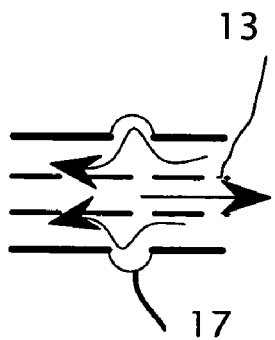
FIG. 13A          FIG. 13B
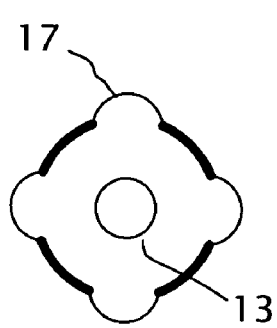
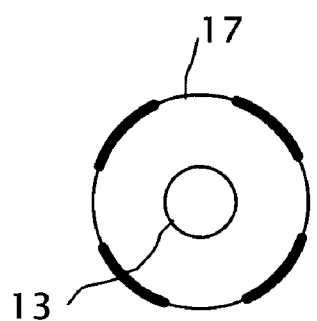
FIG. 14A          FIG. 14B

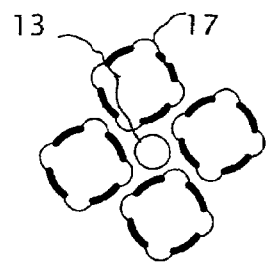
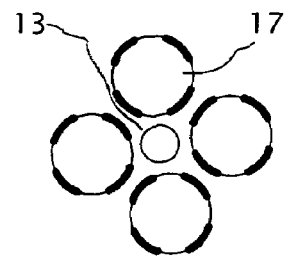
FIG. 15A  FIG. 15B
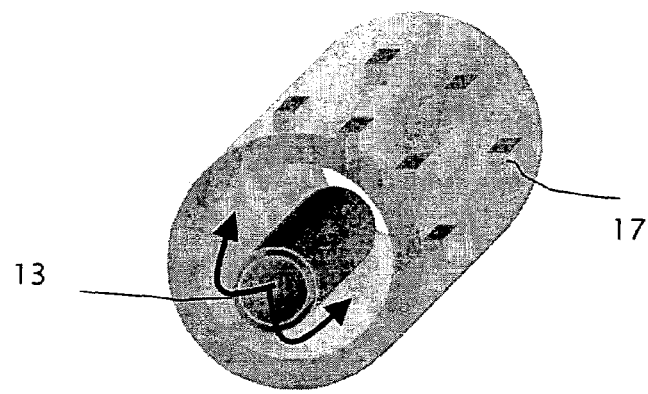
FIG. 16
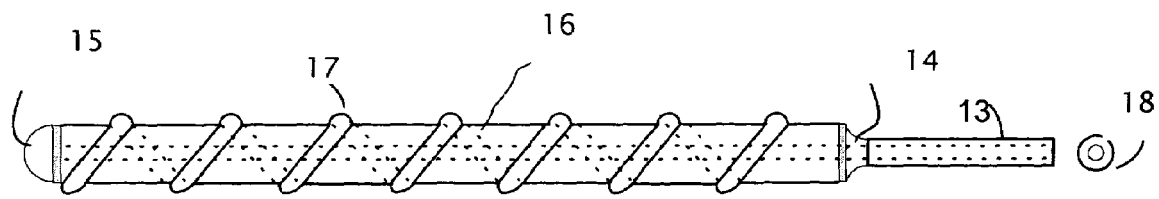
FIG. 17

ACTIVE SURFACE EXCHANGE CATHETER AND METHOD

CROSS-REFERENCE TO RELATED APPLICATION

This application is entitled to the benefit of Provisional Patent Application Ser. Nr. 60/395,842, filed Jul. 15, 2002.

FEDERALLY SPONSORED RESEARCH

Not applicable

SEQUENCE LISTING OR PROGRAM

Not applicable

BACKGROUND OF INVENTION

I. Field of the invention

This invention relates to a medical device used to reduce tissue injury resulting from ischemia, occurring naturally, through trauma or from surgery.

II. Description of Related Art

Tissue in the human body is regulated at a constant temperature of approximately 37 C. An essential part of this regulation is achieved by adequate perfusion of body fluids. Blood perfusion carries out many functions in addition to heat exchange, namely oxygenation of tissue. Without blood perfusion and therefore oxygen delivery, tissue becomes ischemic. For example, normal flow to the brain ranges from 46 to 62 ml/min per 100 grams of brain matter. An accepted critical ischemic threshold is 20 ml/min per 100 grams of brain matter [Reference Cardiovascular Physiology, W. Milnor, pg. 395, 1990]. Unfortunately this threshold is reached during acute ischemic injury, such as stroke, heart attack, or spinal injury. Ischemic thresholds also take place during the course of an initial injury, such as brain swelling after trauma, or reperfusion of occluded coronary/cerebral arteries.

In addition to steps taken to rapidly restore blood perfusion levels above ischemic thresholds, research shows induced hypothermia holds promise for protecting organ tissue from ischemic injury. Among other mechanisms, hypothermia decreases tissue metabolism, concentrations of toxic metabolic byproducts, and suppresses the inflammatory response in the aftermath of ischemic tissue injury. Depending on the time of initiation, hypothermia can be intra-ischemic, post-ischemic, or both. Hypothermic ischemic protection is preventive if tissue metabolism can be closed down. Hypothermia may also enhance recovery by ameliorating secondary tissue injury or decreasing ischemic edema formation. Since the metabolic reduction is less than 10% per degree Celsius, only deep hypothermia, targeting 20–25 degrees Celsius, conceivably provides adequate tissue protection via metabolic slowdown. Secondary tissue injury, thought to be mainly caused by enzymatic activity, is greatly diminished by mild to moderate hypothermia targeting 32–35 degrees Centigrade. As early as 24 hours after onset of ischemia, secondary tissue injury can set off a mass effect with damaging effects on viable surrounding tissues. Late post-ischemic hypothermia decreases edema formation, protecting tissue at risk.

With this in mind, physicians have tried to harness the benefits of hypothermia using a variety of cooling techniques. These techniques vary depending on clinical circumstances. For example, in preventive cooling the goal may be locally applied deep hypothermia, whereas in acute ischemic syndromes, systemic mild to moderate hypothermia may be preferred. The primary focus to this point has been systemic body surface or vascular cooling, only a few concepts have embarked on local, organ specific or cerebrospinal fluid cooling. Systemic cooling has specific limitations and drawbacks related to its inherent unselective nature. For example, research has shown that systemic or whole body cooling may lead to cardiovascular irregularities like reduced cardiac output and ventricular fibrillation, an increased risk of infection, and blood chemistry alterations. Local cooling approaches have been limited by the technological challenges related to developing tiny heat exchangers for small arterial vessels. These vessel inner diameters are 6 mm or smaller.

As a result, the challenge of organ specific cooling is the development of heat exchange catheters that meet the cooling requirements without causing significant physiological disruption. Fortunately, heat exchanger design is not a new science and numerous enhancement techniques have been employed for decades to performance. Two obvious examples include the condenser coil of your home air conditioning system and the radiator of your car. Regardless of the enhancement technique, each approach attempts to achieve one or a combination of the following objectives: 1) reduce the size of the heat exchange device, 2) increase the UA (U, the overall transport coefficient and A, the exchange surface area) to increase the heat exchange rate or reduce the required temperature differences used to drive the exchange process, and 3) reduce the pumping power required to meet a heat exchange target value. (Reference: Principles of Enhanced Heat Transfer, R. Webb, pg. 2, 1994).

For the cooling catheters used to cool organs and not the entire body, the objective is clear: reduce the size of the heat exchange catheter so that in can be placed safely inside an artery while maintaining a adequate heat transfer rate. To understand the design process, consider the following idea. An analogy can be made between electrical behavior and heat transfer; that is the total heat exchange, Q, is proportional to the ratio of the temperature difference (delta T) to the total sum of the heat transfer resistances ($R_{total}$), Q=(delta T/$R_{total}$). This is similar to Ohm's law where the current, I, is proportional to the ratio of the voltage difference to the sum of the electrical resistances.

To select the correct heat transfer enhancement approach for cooling catheters requires balancing two goals: (1) the goal to maximize heat transfer rates to enable sufficient device size reductions and (2) the goal to minimize fluid pressure drop increases to sustain safe organ blood perfusion levels.

Consider the first goal: heat transfer augmentation to minimize size. The first step is to determine the dominant heat transfer resistance and reducing it as much as possible. FIG. 1 shows how the overall heat transfer rate can be affected by changes in heat transfer resistances when we assume a reasonable cooling catheter heat transfer resistance breakdown: 70% of the total resistance comes for the blood-side convective heat transfer resistance, 18% for the coolant-side convective resistance, and 12% from the conductive heat transfer resistance. Looking at the impact of coolant-side resistance (the solid line) on the heat transfer rate ratio (the y-axis), in FIG. 1, we can see that reducing the coolant-side resistance does not provide substantial heat transfer augmentation. To significantly boost cooling catheter performance, the focus should blood side resistance reduction (the dashed line in FIG. 1).

Now consider the second cooling catheter design goal: minimizing pressure drop. Despite the reviewed specifications described for existing cooling catheter patents, heat transfer enhancement is only part of the cooling catheter design challenge. For example if a catheter designer attempts to minimize the dominant heat transfer resistance one may add surface area or rough surfaces to produce turbulent mixing near the heat transfer surface. These attempts likely will boost the heat transfer performance significantly, but they will also likely reduce perfusion rates because of an increased pressure drop levels across the enhanced surfaces. FIG. 2 shows an example of a cylindrical cooling catheter design. In this example the ratio of the cooling catheter radius to the vessel radius is shown as $R_i/R_o$. If we assume that the heart is analogous to a single speed pump, as the ratio of radii increases the pressure drop across the catheter increases, until the heart cannot overcome this hydraulic resistance and perfusion rates fall. At that point the flow past the cooling device decreases and the heat transfer performance also rapidly falls. This example demonstrates that a single-minded attempt to increase heat transfer rates can reduce organ perfusion levels.

Heat transfer enhancement techniques can be broken down into two broad categories: (1) passive techniques and (2) active techniques. Related endovascular cooling catheter patents to this point have relied solely on passive transport enhancement techniques, where a fixed or static cooling catheter is placed inside a stagnant or moving body fluid. FIG. 2A shows a passively enhanced cooling catheter inside a blood vessel (U.S. Pat. No. 6,096,068, Dobak et al. 2000). Unlike most active enhancement techniques, the heat exchange surfaces for these passive enhancement techniques remain motionless during the heat transfer process.

Consequently, passive techniques are transport enhancement approaches that do not add mixing energy to the fluid system of interest. The energy used to create enhanced performance is taken from or drawn from the stored hydraulic energy involved in the exchange process. They are particularly effective when fluid pumping power or hydraulic energy is not limited or prohibitive in cost. The approach involves adding surface area and or inducing turbulence adjacent to the effective exchange surface area (FIG. 2A). These approaches are also used throughout the heating and air conditioning industry where fluid pumping power or hydraulic energy can easily be increased. This differs, however, from the human body where physiological constraints naturally limit the hydraulic energy or fluid pumping power. In turn, aggressive passive enhancement techniques, particularly in small vessels, like those that lead to individual organs like the brain, spinal cord, or kidney, are likely to lead to substantial blood side pressure drops that may affect cardiac output and or organ perfusion.

U.S. Pat. No. 6,096,068, by Dobak and Lasheras (Aug. 1, 2000) describes a metallic cooling catheter used to exchange heat inside the body. To enhance heat transfer, articulated segments are used to increase surface area and induce turbulence, a classic passive enhancement technique. Clockwise and counter clock-wise segments mix the thermal boundary layer in highly pulsatile flow inside the carotid artery, creating a turbulence intensity, I, of greater than 0.05 (1 equals the RMS velocity fluctuation/mean velocity). This patent, however, does not address the critical issue of device blood-side pressure drop, the inherent cost resulting from a heat transfer enhancement technique. In fact the turbulence generated with devices like these does not come without some fluid energy cost (FIG. 2A). In this case, fluid energy is lost through shear stresses in the fluid, also called viscous dissipation, where kinetic energy is irreversibly converted to thermal energy or molecular motion. The end result is increased pressure drop. So while the aggressive clockwise and counter-clockwise segments may be effective in large inner diameter vessel like the vena cava, used for systemic cooling, aggressive passive enhancement techniques if used in the smaller vessels, like the common carotid, are likely to lead to brain perfusion reductions that can worsen the ischemic injury to the brain. Furthermore, aggressive techniques like these when in contact with the vascular wall may disrupt unstable plaque and generate emboli and create further ischemic injury, especially if there is not a method to avoid catheter surface to vessel wall contact. Consequently, turbulence intensity alone is not a sufficient indicator of an effective endovascular heat exchanger for small arteries.

There are two more concerns with this patent (U.S. Pat. No. 6,096,068, Dobak and Lasheras (Aug. 1, 2000)): a) the coolant side pressure drop is large, equal to five atmospheres or 3800 mmHg; a catheter fracture failure would lead to a high pressure liquid jet impinging upon the vascular wall and b) the articulated segments are prone to thrombus generation due to blood flow stagnation zones that will inherently be established along the catheter surface.

Two other patents by Gobin et al., U.S. Pat. No. 6,126,684 (Oct. 3, 2000) and Dae, U.S. Pat. No. 6,231,594 (May 5, 2001) address endovascular cooling with inflatable static balloons. By static balloons we mean the balloon walls that remain motionless once they are inflated and the heat exchange process has begun. This approach is useful for device insertion and for increased exchange surface area when the cooling action is begun. Gobin et al. uses multiple balloon chambers with a coolant distribution technique to ensure a maximum temperature difference between coolant and blood flow. The multiple chambers help maintain catheter flexibility. The Dae patent, similar to Gobin et al., uses multiple balloons twisted into a helix with separate cooling pathways. In both of these designs heat exchange effectiveness is driven by two factors: 1) the increased heat exchange surface area (a passive enhancement approach) and 2) the carefully circulated coolant pathways. This is in contrast with the Dobak and Lasheras patent (U.S. Pat. No. 6,096,068 Aug. 1, 2000) discussed above that relied primarily on turbulence intensity boosts for improved heat transfer. Furthermore, in both of these balloon catheter patents information is not provided on the impact of device inflation on normal blood flow nor is there information provided on the internal coolant pressure. In addition, both patents do not address the issue of blood hemodynamics leading to flow stagnation zones on the catheter that are likely sites for thrombus generation.

In yet another patent by Keller et al., U.S. Pat. No. 6,264,679 (Jul. 24, 2001) a third approach is taken for endovascular cooling. Using small hollow fibers, coolant is passed from one manifold to the next. The arrangement is similar to a tube and shell heat exchanger used throughout large cooling systems such as chillers. This approach attempts to maximize the available heat exchange surface area and maintain a well-distributed coolant to ensure the maximum temperature difference between the coolant and the blood. This patent also does not address the fundamental design challenge of avoiding increased fluid pressure drops nor does it address the concern of blood stagnation zones inside the hollow fiber bundle.

In summary these endovascular cooling techniques mentioned above have one or more of these disadvantages.

a) In general, these designs have low heat exchange surface area to device volume ratios. This leads to deleterious vessel occlusion characteristics, particularly with smaller arterial blood vessels, increasing the chance for further ischemic injury.

b) The designs are likely to have blood flow stagnation zones, likely sites for thrombus formations. There are many crevices within each design that are not washed effectively.

c) In general, these designs have high internal coolant pressures because the working fluids must be circulated at high rates through small passageways to maintain high heat transfer effectiveness. In fact, in some cases this internal pressure is as high as 3800 mmHg gauge pressure, making device rupture a potentially harmful failure mode.

d) The designs do not state a method to maintain the exchange catheter orientation inside the center of a blood vessel to avoid emboli generation and to maintain maximum exchange performance. This is a particularly important problem when the device size is nearly equal to the blood vessel.

e) These designs do not offer the ability to transfer therapeutic drugs or physiological gases as needed simultaneously with the heat transfer process. They do not explore the idea of using porous materials to transfer heat and mass.

While endovascular heat exchangers have not employed active mixing to augment transport, some other applications are noted. Reeder et al. U.S. Pat. No. 6,217,826 (Apr. 17, 2001) and Borovetz et al. U.S. Pat. No. 6,348,175 (Feb. 19, 2002) each describe the value of active mixing enhancement for a blood pump design. Furthermore, Hattler et al. U.S. Pat. No. 5,501,663 (Mar. 26, 1996), describes an endovascular mass exchanger that uses active mixing. It uses a balloon with porous fibers to enhance mass transfer between a low viscosity blood gas flowing within the fibers and the blood flow surrounding the fibers. Krantz et al. U.S. Pat. No. 5,626,759 (May 6, 1997) also uses active mixing for blood oxygenation outside the body. In this patent, blood flows inside hollow fibers that are vibrated in an axial direction held inside a bedside container.

SUMMARY

A catheter for insertion into a body cavity for contact with a body fluid comprises one or more tubes making surface contact with the body fluid. A working fluid, or fluids, is circulated internally through the tubes for interaction with the body fluid through the tube surfaces. For enhancing such interaction, a working fluid drive system provides various means for adding energy to the tube surface and or the surrounding body fluid. These enhancement measures induce boundary layer disruption or secondary flows at the tube surfaces, reducing the thickness of the thermal and concentration boundary layers in the fluid space adjacent to the tube surfaces, resulting in improved exchange rates In many embodiments the working fluid has two purposes: 1) to act as a vehicle to carry energy and mass through the drive system, and 2) to add energy to exchange surfaces and reduce fluid boundary layer thicknesses.

In one embodiment, an elongated tube or several elongated tubes with nonuniform compliance and a working fluid drive system are used to cause boundary layer disruption at the tube surface. The working fluid drive system creates periodic changes in internal working fluid pressure resulting in tube surface deformation and boundary layer disruption. Surface designs for nonuniform compliance tubes may be chosen to augment body fluid motion in an axial direction using a screw-like action.

In another embodiment, a directional cycling or shuttle working fluid drive system is used to dispense and remove working fluid from a bundle of tubes in a periodic fashion. The directional cycling characteristic of the drive system has the effect of creating tube surface vibrations in both an axial and a radial direction. Again, these vibrations are used to disrupt and reduce adjacent fluid boundary layer thicknesses.

In another embodiment, a small turbine is used to rotate a bundle of tubes. Rotation in this embodiment creates boundary layer disruption near the tube bundle surfaces. The turbine converts the hydraulic energy provided by the working fluid drive system into tube bundle rotational energy.

In another embodiment, an elongated balloon is provided in parallel with an encircling bundle of tubes. The working fluid drive system in this embodiment pulsates the inner balloon and circulates the working fluid through the tube bundle. Balloon pulsation is used to disrupt and reduce adjacent boundary layer thicknesses.

In still another embodiment, the tube surfaces or other portions of the exchange catheter surfaces are porous. Together with the working fluid drive system, this porous characteristic enables two separate and controllable modes of heat and mass transfer: 1) direct infusion of the working fluid into the body fluid, and 2) surface heat and mass exchange found with nonporous exchange surfaces. Furthermore, a sealed penetration point at end of the catheter is described that allows interconnection between an exchange catheter and a distal protection filter catheter, enabling correct alignment of the exchange catheter inside a blood vessel.

DRAWINGS

In the drawings, closely related figures have the same number but different alphabetic suffixes.

FIGS. 12A and 12B shows a cross sectional view of the nonuniform compliance exchange catheter at both high and low pressure periods of the working fluid pumping cycle.

FIGS. 13A and 13B shows another cross sectional view along the axis of the nonuniform compliance exchange catheter at both high and low pressure periods of the working fluid pumping cycle.

FIGS. 14A and 14B shows a cross sectional view of an alternative design for the nonuniform compliance exchange catheter at both high and low pressure periods of the working fluid pumping cycle.

FIGS. 15A and 15B shows another cross sectional view of a multi-tube design for the nonuniform compliance exchange catheter at both high and low pressure periods of the working fluid pumping cycle.

FIG. 16 shows a three-dimensional view of a section of a nonuniform compliance catheter during the high pressure period of the working fluid pumping cycle.

FIG. 17 shows a variable compliant auger-type exchange catheter during a high pressure period of pressure cycling.

Figure 1:
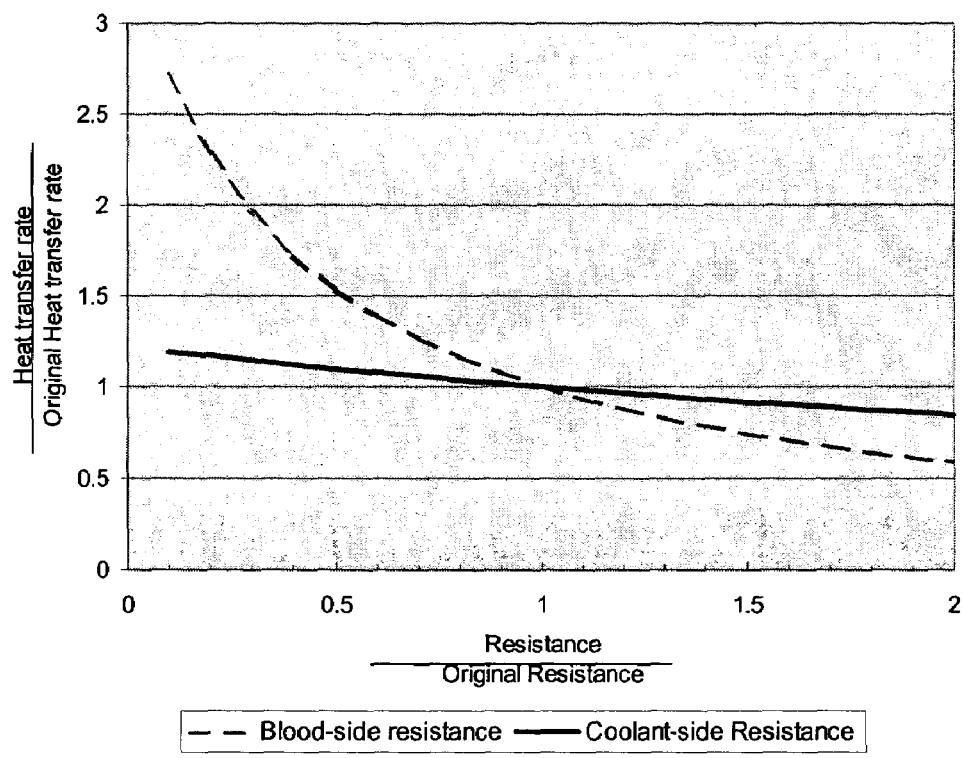
FIG. 1 shows how the overall heat transfer rate is affected by changes in coolant-side and blood-side heat transfer resistances.
Figure 2:
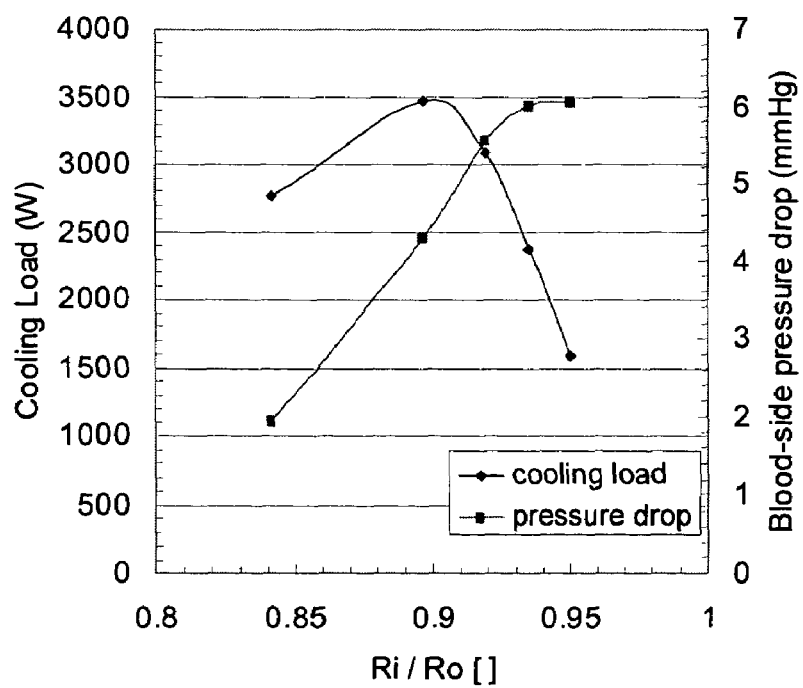
FIG. 2 shows how heat transfer and pressure drop vary for a concentric tube heat exchanger design as a function of the radii ratio.
Figure 2A:
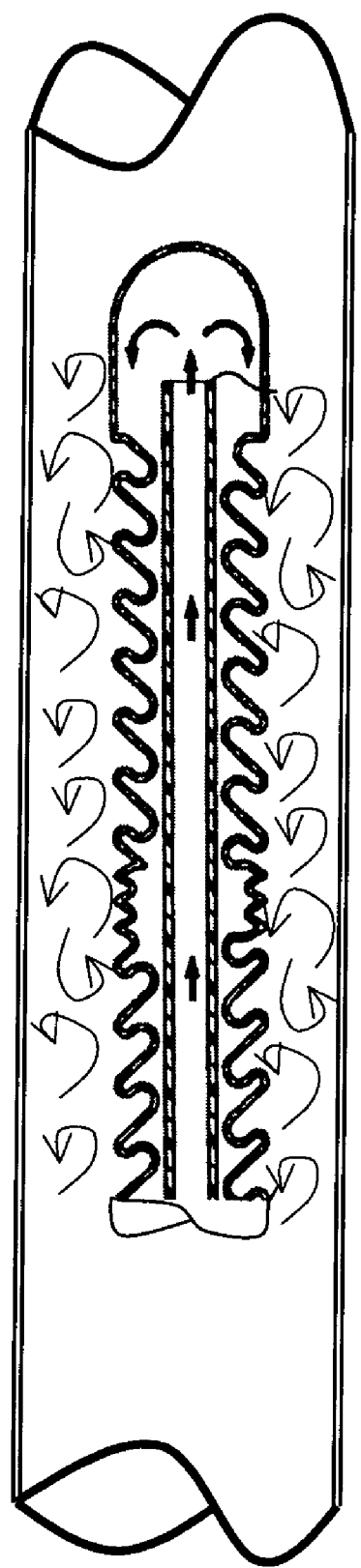
FIG. 2A shows a passively enhanced cooling catheter with static exchange surfaces.

REFERENCE NUMERALS IN DRAWINGS 1. exchange catheter
2. temperature sensing port
3. pressure sensing port
4. catheter connecting tubing
5. the heat and mass exchanger
6. the outlet for the working fluid used to exchange heat and mass, including temperature sensing port
7. the inlet for the working fluid used to exchange heat and mass including temperature sensing port
8. fluid or pharmaceutical injection or removal port.
9. liquid pump
10. pump drive
10A. solenoid valve for flow pulsation.
11. system control and monitoring console
12. additional active mixing drive system, e.g. a balloon pulsation system
13. delivery catheter
14. proximal manifold
15. distal manifold
16. nonuniform compliant tube
17. dynamic surface component
18. delivery catheter inlet view
19. axial vibration compliant tubing
20. distal collection balloon
21. hollow fiber or compliant tube
22. proximal turbine manifold
23. sealed bearing
24. internal active mixing balloon
25. single or multiple orifices for infusion
26. distal protection filter and or guide wire interconnection

DETAILED DESCRIPTION

When a physician faces a patient that is in endanger of ischemic injury, a fundamental objective is the safe return to acceptable blood perfusion levels. While the core infarcted tissue that is immediately affected by perfusion reduction may not be salvageable there exists a region called the ischemic penumbra that is salvageable. This may involve altering cardiac function and or removing a thromboembolic occlusion that prevents sufficient perfusion. Drugs called thrombolytics are used to chemically remove the occlusion.

Two additional approaches for treating ischemic injuries also show promise. The first approach involves more chemical intervention with neuropreservative drugs. These drugs address the biochemical process behind cell death resulting from ischemic perfusion levels. The second approach is the use of induced hypothermia to alter metabolism and biochemical transport behavior. This invention application describes methods to induce localized or organ specific cooling.

The previous patents described above, with catheters having typical sizes ranging from 3 to 4.5 mm in diameter, attempt to provide rapid endovascular cooling using only passive heat transfer enhancement techniques. While these devices may cool effectively, they do not address the central problem of the device's impact on perfusion, particularly in small vessels like the common carotid artery. The invention we describe here addresses that critical problem and others.

Figure 3A:
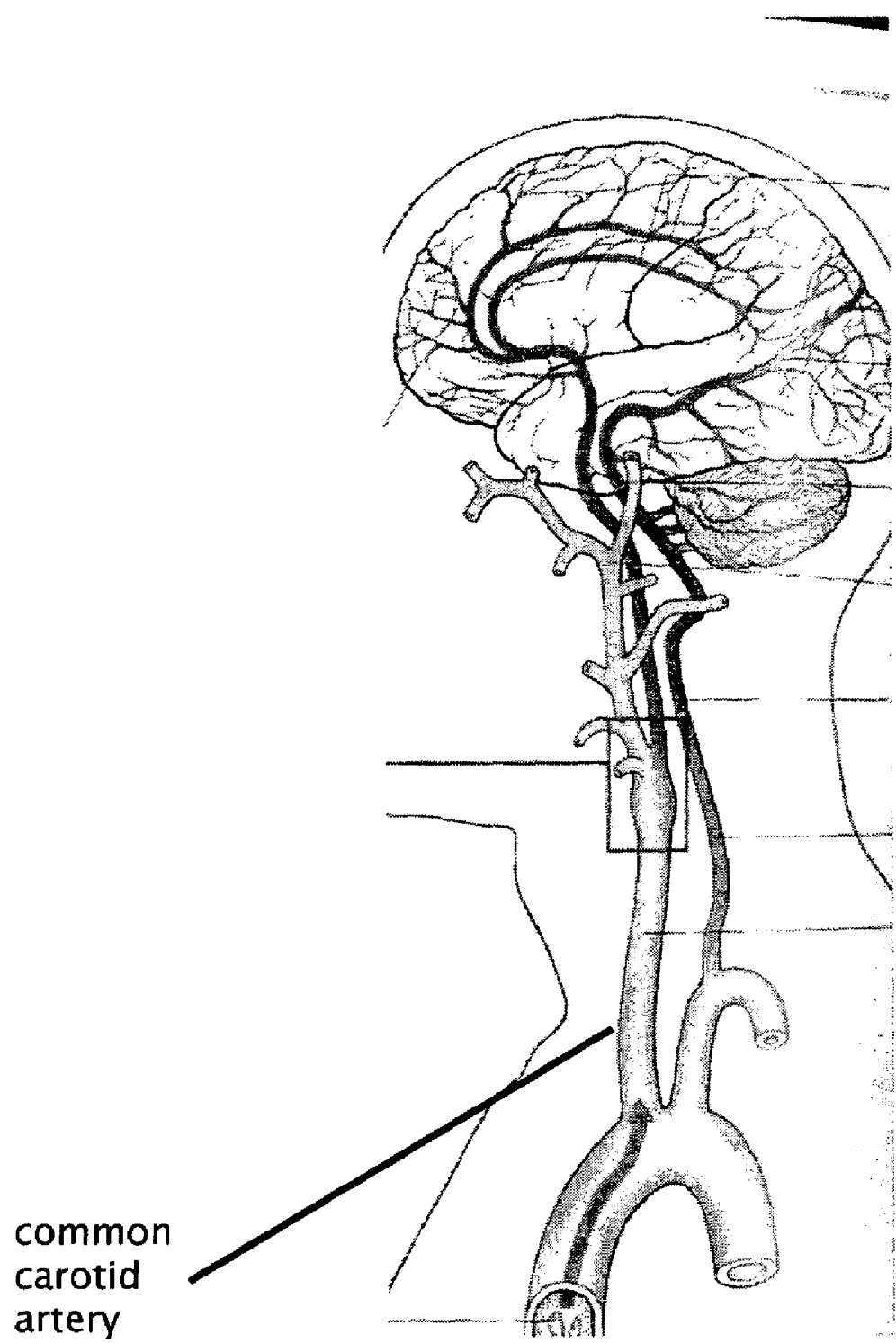
FIG. 3A shows the vascular system inside the head and neck.
Figure 3B:
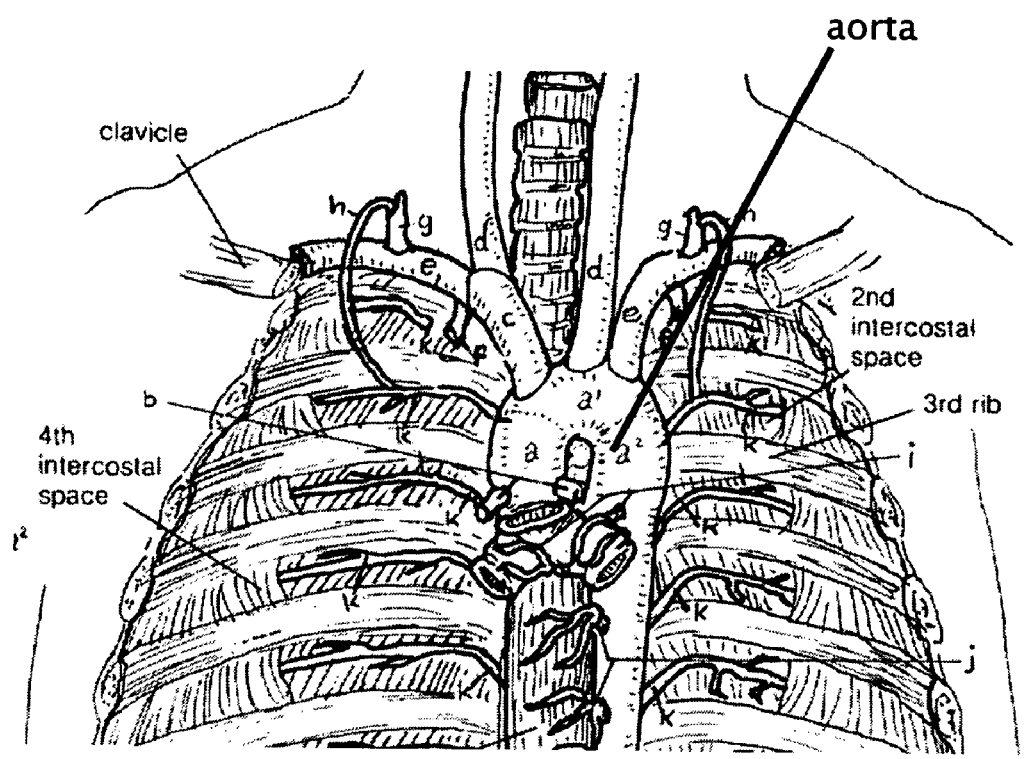
FIG. 3B shows the aorta and nearby arteries.
Figure 4:
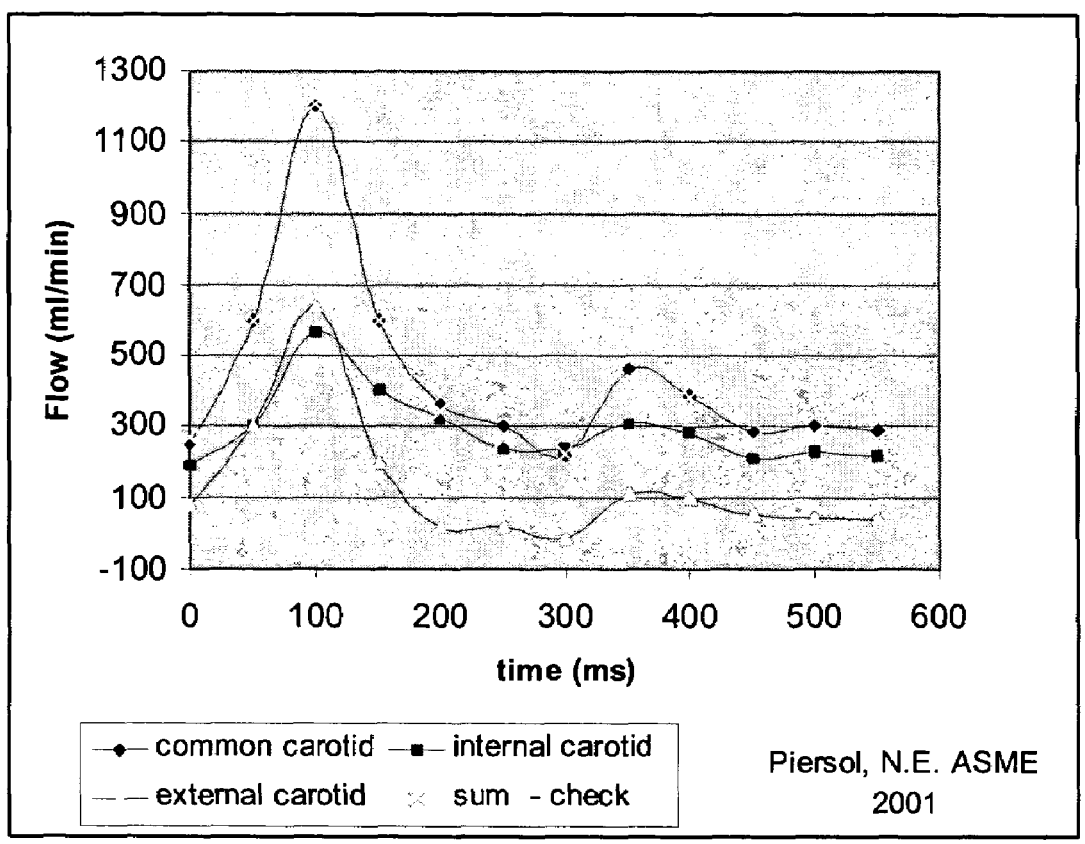
FIG. 4 shows the flow profile inside the carotid artery.

FIGS. 3A and 3B show the physiological landscape where endovascular cooling catheters are used. FIG. 3B shows the aorta and nearby arteries. FIG. 4 shows the pulsatile flow behavior inside the carotid artery during a cardiac cycle. Only during a small portion of the cardiac cycle is the flow inside the common carotid artery turbulent, about 20% of the time. Therefore, during a majority of the cardiac cycle the flow inside the common carotid, while pulsatile, is considered well organized or laminar. The typical mean flow in a common carotid artery ranges from 250 to 350 ml/min.

Consider the common carotid artery (FIG. 3A) for local induced hypothermia. Common carotid inner diameters range from 6 to 8 mm and its length ranges from 8 to 12 cm. In the vena cava, where the previously described devices are typically used for systemic cooling not local cooling, inner diameters may range from 20 to 25 mm. Because of this vessel size difference, heat transfer design optimization is significantly less critical. In other words, the process of optimizing the benefit of heat transfer improvement to the cost associated with pressure drop increases is not as important for cases where the vessel size is substantially larger than the cooling catheter. On the other hand, when the vessel sizes are smaller, localized cooling or organ specific cooling requires this optimization if safe levels of blood perfusion rates are to be maintained during the cooling process.

Before describing our embodiments and the methods that address this fundamental design optimization challenge, a review of heat transfer physics surrounding an endovascular cooling process is helpful.

When a cooling catheter is placed inside a blood vessel heat is first transferred by convection from the warm blood to the cool catheter exchanger surfaces. These exchanger surfaces then transfer heat by conduction across the material thickness from the outer surface in contact with the blood to the inner surface in contact with the cool working fluid. Finally heat is transferred from the inner surface of the catheter to the working fluid, again using convective heat transfer. An in-depth analysis of this heat transfer process shows that in most cases the dominant resistance for heat transfer is blood side convection, not the other resistance terms, coolant side convection and conduction through the catheter wall (FIG. 1).

To reduce this dominant resistance it is helpful to understand the convective resistance relationship where convective resistance, $R_{conv}=1/h_{blood}A_{blood}$, where $h_{conv}$ is the blood side convective heat transfer coefficient and A is the blood side exchange surface area. Therefore, to reduce this resistance or in other words provide heat transfer enhancement we can either increase $h_{blood}$ or $A_{blood}$ or both.

To gauge the effectiveness of a particular enhancement a term called an efficiency index, $_e$, is used where $_e=(j/j_s)/(f/f_s)$ and j=Colburn j factor, a dimensionless heat transfer coefficient, and f=Fanning friction factor, a dimensionless pressure drop term. The subscript s indicates the value for a smooth or non-enhanced surface.

Most passively enhanced surfaces like those found in earlier described patents and like those used in cooling equipment like air conditioners have efficiency indices between 0.9 and 0.8 (Reference: Principles of Enhanced Heat Transfer, R. L. Webb, p. 50, 1994). In other words, for well-performing passive enhancements there is nearly a one to one relationship between the increases in heat transfer rates and the resulting increases in pressure drops. This does not pose a problem with most heat exchanger applications, but it does pose a problem with endovascular heat exchange. In fact, the efficiency index is closer to 0.5 for laminar flow conditions. Consequently for every percentage increase in heat transfer, the pressure drop increases at twice that percentage. Therefore, while passive enhancement approaches alone may increase heat transfer by inducing localized turbulent mixing near a heat exchange surface, the viscous dissipation of these turbulent mixing eddies usually leads to substantial pressure drops and flow reductions if pumping power can not be increased.

To address this fundamental design problem, we are applying a hybrid enhancement approach, utilizing both active and passive enhancement techniques. The active enhancement concepts used with our embodiments discussed here add energy to either the fluid—exchanger surface interface or the fluid itself, disrupting thermal and concentration boundary layers that lie adjacent to the exchange catheter surfaces. By disrupting these boundary layers the boundary layer thicknesses are reduced and since the convective heat and mass transfer is inversely proportional to boundary layer thickness, higher rates of transport occur. Since the energy used to reduce these boundary layer thicknesses is primarily drawn from the active enhancement technique and not drawn solely from the hydraulic energy of the body fluid (as is the case with passive enhancement techniques), devices can be made sufficiently small to fit inside arteries, while achieving sufficient heat exchange rates and safe perfusion levels.

To achieve this outcome, two devices are needed: a working fluid drive system that provides the energy to drive active enhancement and an exchange catheter that provides the interface between the working fluid and the body fluid.

Figure 5:
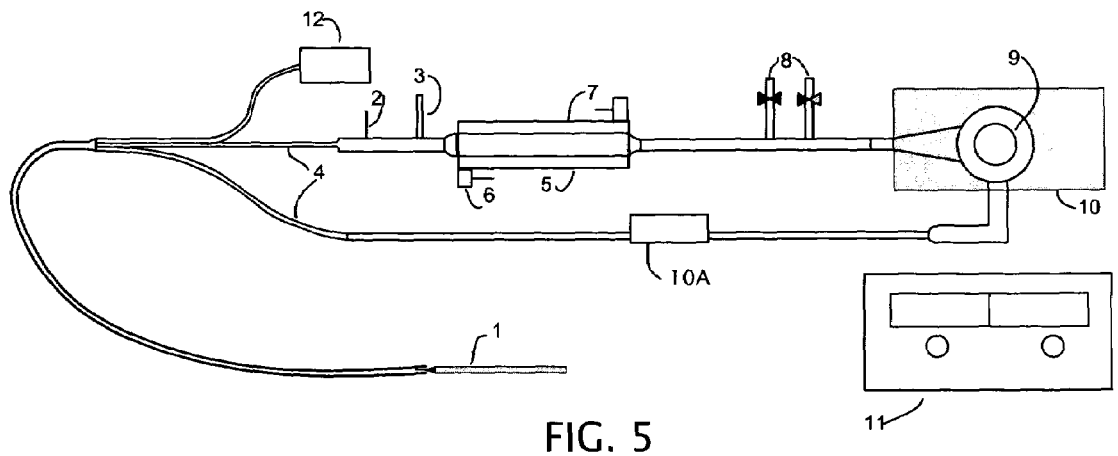
FIG. 5 shows a working fluid continuous flow circulation system or drive system.

FIG. 5 shows the major components of a working fluid drive system or circulation system together with an exchange catheter. The primary purpose of this system is threefold: 1) pump the working fluid into the exchange catheter, 2) condition the working fluid to the target properties that enable target exchange rates, 3) provide a method to disrupt fluid boundary layers during the exchange process. Looking more closely at FIG. 5, interconnecting tubing, 4, connects a working fluid circulation system to the exchange catheter, 1, described hereinafter. Upstream of this connection are two ports: a temperature sensing port, 2, and a pressure sensing port, 3. Upstream of these ports is a compact heat and or mass exchanger, 5, that conditions the working fluid to a proper temperature, gas concentration, and or drug concentration. To simplify and reduce the complexity of this component, the heat exchanger may be of an air-cooled design if performance levels are sufficient. A standard blood oxygenator may be used for mass exchange. A secondary loop inlet port, 6, and outlet port, 7, allow connections between a working fluid circuit and a secondary conditioning circuit. Temperature and pressure probes may also be placed in these ports. Additional ports for monitoring working fluid characteristics are also available, 8. A primary working fluid pump head and motor, 9 and 10, circulates a working fluid as dictated by an overall control system, 11. This pump and motor may be used to induce working fluid pulsations or instabilities. An example of such a pumping system is a MasterFlex L/S computer controlled peristaltic pump. In addition, a solenoid valve or electric valve, 10A, may also be used to cause working fluid pulsations or instabilities. A Cole-Parmer two-way pinch valve may be used. These valves have a response time that ranges from 35 milliseconds to 50 milliseconds, depending upon the model chosen. These valves allow maximum pulsation frequencies ranging from about 20 Hz to 30 Hz. User inputs specify target body fluid temperature, target body fluid concentration, and the rate of heat and mass exchange.

Figure 8:
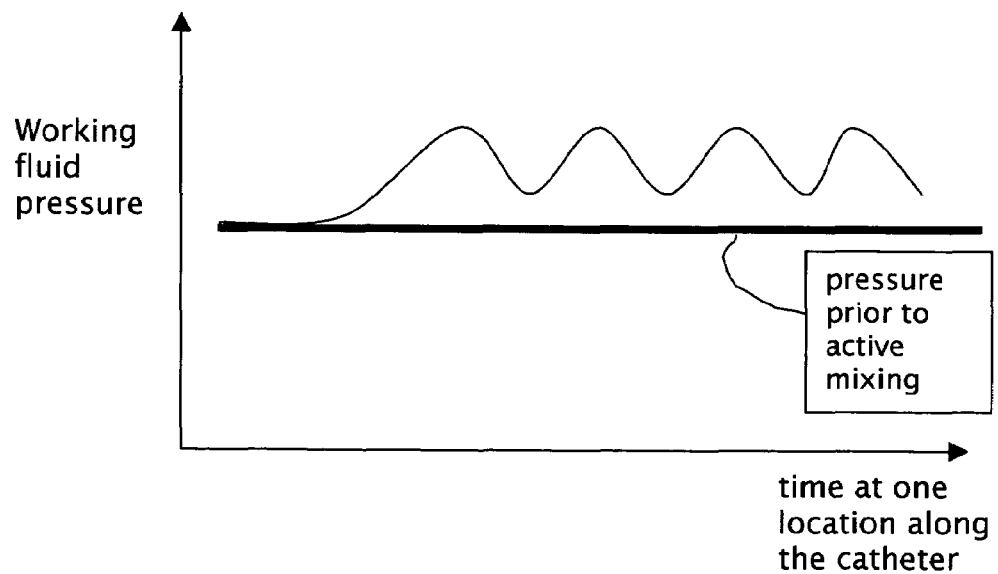
FIG. 8 shows how pressure may oscillate at one location along the cooling catheter.

The control system, together with user inputs, operates the entire system, including primary and secondary circulation loops. The control system automatically adjusts active mixing parameters such as the frequency of pulsation and the amplitude of pulsation. FIG. 8 shows the pressure pulsation at one location inside an active mixing exchange catheter. Additional parameters that influence the pulsation waveform may also be adjusted to optimize the heat transfer benefit to the pressure drop cost. The control system uses standard electrical components, a real-time operating system, embedded software, wireless communication hardware, and algorithms found in typical feedback and control systems.

Figure 6:
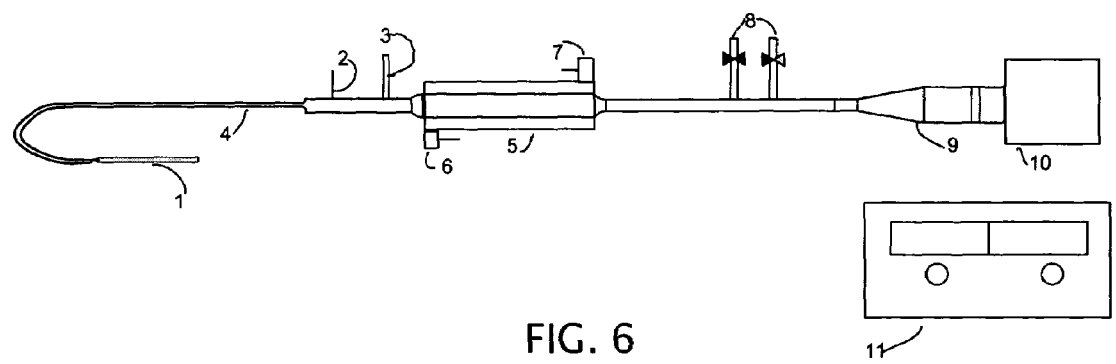
FIG. 6 shows a directional or shuttle working fluid drive system.
Figure 9:
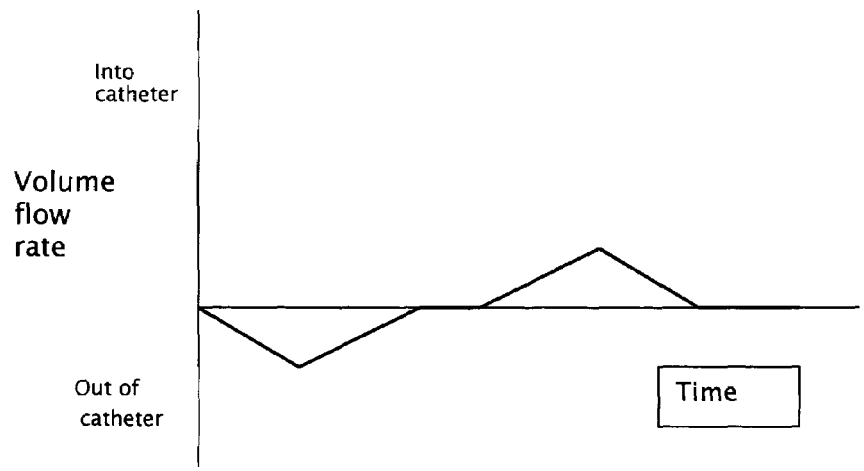
FIG. 9 shows the working fluid flow behavior using the shuttle drive system, FIG. 6.

FIG. 6 shows a similar system to that described in FIG. 5, except that this system shuttles the working fluid to and from the exchange catheter instead of using continuous circulation. The pump head and motor assembly, 9, and 10, is any pump that allows continuous cycling of forward and reverse flow. This overall system is used with shuttle-flow type exchange catheters described below. The working fluid flow profile for this shuttle system is shown FIG. 9. To create maximum exchange surface to boundary layer interaction, the control system will create waveforms like that shown in FIG. 9.

Figure 10:
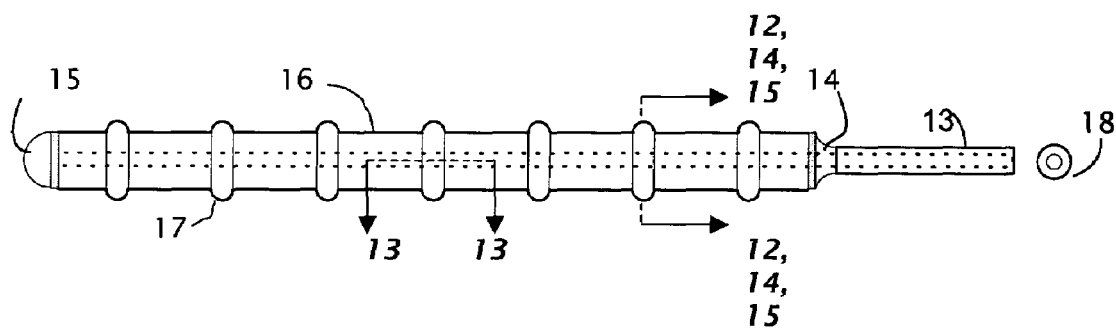
FIG. 10 shows an exchange catheter with nonuniform compliance during a high pressure period of pressure cycling.
Figure 11:
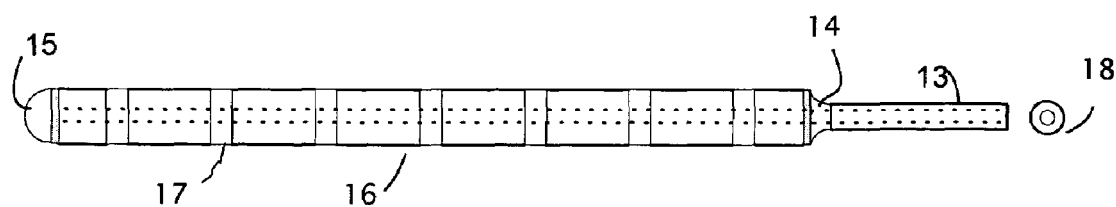
FIG. 11 shows an exchange catheter with nonuniform compliance during a low pressure period of pressure cycling.

FIG. 10 shows a preferred embodiment of the exchange catheter. This exchange catheter may have a range of sizes depending upon the clinical application. The outer diameter of the exchanger catheter may range from 2 to 6 mm and lengths ranging from 4 to 10 cm. There are five major components to the exchange catheter: 1) a multi-lumen delivery catheter that carries the working fluid to and from the exchange catheter, 13, 2) a proximal working fluid manifold, 14, 3) a distal working fluid manifold, 15, 4) nonuniform compliant tube, 16, and 5) a dynamic surface component, 17.

The multi-lumen delivery catheter, 13, 18, is sized to allow sufficiently rapid circulation of the working fluid and therefore maximum internal heat and mass transfer coefficients without excessive working fluid pressure drops like those found in earlier described patents. The multi-lumen delivery catheter enters the proximal manifold, 14, and extends the length of the exchange catheter to the distal manifold, 15. It is made of a polymer with low thermal conductivity to minimize heat transfer between the incoming and outgoing working fluid. Multi-lumen catheters like these are readily made with existing polymer extrusion techniques. They can be easily purchased from manufacturers like Zeus Industrial Products Inc., in Orangeburg, S.C.

The distal manifold, 15, evenly distributes the inlet working fluid to the annulus created between the delivery catheter and the exchange surfaces (FIG. 12). The distal manifold outer surface is smooth to avoid internal vascular damage or emboli generation. The distal manifold inner surface provides a smooth transition to turn the working fluid 180 degrees since in most embodiments the working fluid first travels the length of the exchange catheter before turning and entering the annulus region where it is in contact with nonuniform compliant tube, 16. This flow configuration is done to provide a counter flow exchange process with the working fluid flowing in the opposite or counter direction of the body fluid. Counter flow heat exchanges maintain larger temperature differences along a coolant path, enabling higher heat transfer rates. The distal manifold is made of biocompatible polymer like polypropylene, Delrin, or a urethane. Exchange surfaces, 16, are connected to the distal manifold in a process called potting. In this process the tube(s) are connected to the distal manifold, 15, and proximal manifold, 14, using standard polymer adhesives such as epoxies and cyanoacrylates.

The tube material, 16, is polypropylene, polyurethane or similar flexible polymer. These nonuniform complaince tubes may be manufactured easily using timed dipping of polish metallic mandrels into and out of containers of liquid polymer. Over time these dipping steps accumulate tube wall material on the mandrel. When the wall thickness is about 0.1 to 1.0 mm thick, the polymer may be removed from the mandrel with warm water, soap, and perhaps a glycerol water mixture. Variation in dipping procedures and mandrel design allow the alteration of tube wall thickness and the resulting tube compliance properties. As an alternative, tubes like these could be purchased from companies like Advanced Polymers Inc. in Salem, N.H. Advanced Polymers Inc. makes custom tubes and balloons for medical applications and they have proprietary methods for producing nonuniform compliance tubes.

The tube surface, like all of blood contacting surfaces, are coated to avoid thrombus generation. Although, due to the inherent fluid mixing generated with each active enhancement technique described below, blood stagnation zones are minimized significantly. Coatings like covalently bonded heparin are used. In addition, outer surface roughnesses, a passive enhancement technique, may also be added to promote outer boundary layer disruption and subsequent transport enhancement. Sand grains together with a polymer adhesive may be used to achieve transport enhancement.

During operation the preferred embodiment (FIG. 10) circulates the working fluid at desired conditions from the continuous working fluid drive system (FIG. 5) to delivery catheter, 13. From the delivery catheter the working fluid first travels to the distal manifold, 15, then turns 180 degree around and travels down the annulus that is created between the delivery catheter and the exchanger surfaces, 16, finally reaching the proximal manifold, 14, and the delivery catheter annulus. From the deliver catheter annulus, the working fluid travels through the interconnecting tubing of the drive system to the electrical valve, 10A, and the pumping system, 9 and 10. From the pumping system, the working fluid is reconditioned and monitored before returning back to the exchange catheter. This cycle is repeated and controlled by the control system, 11. The control system also controls the active mixing parameters such as the operating flow rates, the mean operating pressures, the frequency of pressure oscillations, and the amplitude of operating pressures.

Figure 7:
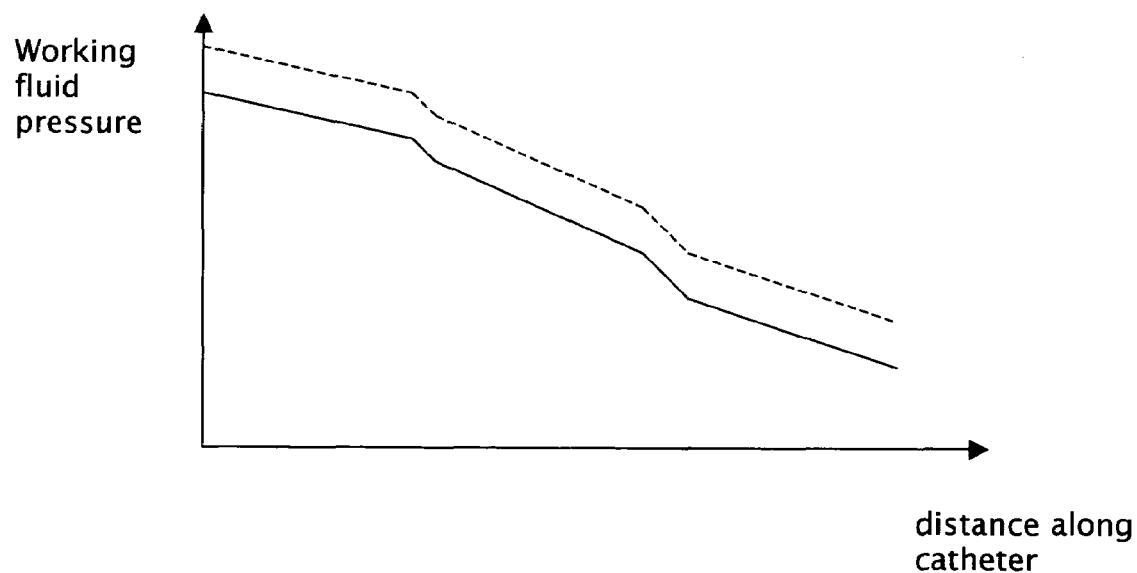
FIG. 7 shows how pressure may vary along the length of a cooling catheter.

FIG. 7 shows the pressure variation along the working fluid pathway from the exit of the drive system to the exit of the exchange catheter at an instant in time. The required amount of pressure variation is determined by the compliant characteristics of the nonuniform compliant tube(s), 16. FIG. 8 shows the pressure variation with time at a particular point along the exchange catheter. The movement of the electrical valve, 10A, and the control system, 11 create the frequency and amplitude of periodic pressure variations. Typical frequencies are 1 to 20 Hz with amplitudes ranging from 10 to 50 percent of the mean operating pressure. FIGS. 12 through 16 show the effect of periodic pressure variations on various exchange catheter configurations, from single tube to multiple tube bundles. With active enhancement these surface contours oscillate during the exchange process causing the relatively stable boundary layers to become unstable and reduce in thickness. FIG. 16 shows a three-dimensional cut-away view of the exchange catheter at the distal manifold during a high pressure pulse. The arrows show that the working fluid first travels down the length of the catheter and then turns 180 degrees to travel down the nonuniform compliance tube.

Figure 18:
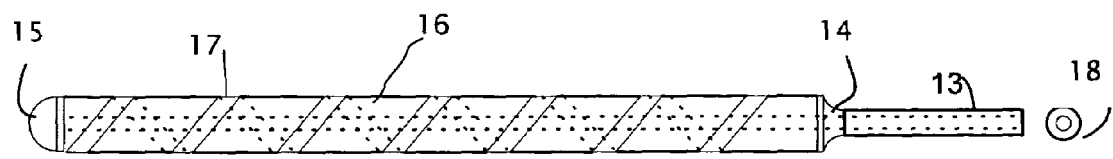
FIG. 18 shows a variable compliant auger-type exchange catheter during a low pressure period of pressure cycling.

FIGS. 17 and 18 show another embodiment using nonuniform compliant tubes. In this embodiment, an auger-type design is used to not only disrupt local boundary layers near the exchange catheter surface, but also motivate flow in the axial direction. With each periodic pressure rise the surface contours create a twisting action that pushes fluid along the natural direction of body fluid flow. To create the desire effects working fluids for this embodiment may travel in a parallel direction with the body fluid.

Before leaving this preferred embodiment description it should be noted that other methods for surface movement can be used. Embodiments shown in FIGS. 10 and 16 also alter their exchange surface geometry with the use of electroactive polymers, particularly ionic electroactive polymers or polymer—metal composites. In these cases small voltages are applied to the exchange catheter to create small but rapid, 1 to 10 Hz, movements along the exchange catheter surfaces.

Figure 19:
FIGS. 19 and 19A show a shuttle-type exchange catheter and fiber potting
Figure 19A:
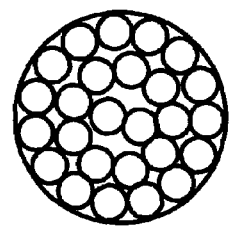

In another embodiment shown in FIG. 19 hollow fibers that can be used. They range in size from 0.2 mm to 0.6 mm in terms of outer diameter. Celgard Inc, Charlotte, N.C. is a well known supplier of hollow fiber membranes. To create the manifolds, 20 and 14, fibers are secured to a polymer ring like Delrin, using readily available cyanoacrylate epoxies. FIG. 19A shows a cross sectional view of this potted region. A tapered section is then created to link the potted region with the delivery catheter, 13.

The embodiment shown in FIG. 19 is considered a shuttle exchange catheter. This catheter employs the working fluid shuttle system shown in FIG. 6. The purpose of the external or distal collection balloon, 20, made of polyurethane or similar polymer, is to act as a reservoir for the working fluid during push and pull strokes of the shuttle system. There are two characteristics that can be used to achieve active mixing. First the wall thickness of the hollow fibers or tubes, 16 (made of polypropylene or similar polymer) of this design can be selected such that the filling and emptying strokes of the shuttle system (FIG. 6) produce movement in the radial direction. Second, an axial vibration compliant tubing, 19 can be used to move the exchange surfaces in a parallel direction with the working fluid flow. Advanced Polymers Inc., Salem N.H., provides manufacturing capabilities that enable dissimilar polymer fusing. With each pull and push of the working fluid out of and into the exchange catheter axial vibrations occur. Again both of these active mixing techniques cause thermal boundary layer disruption in the blood flow, augmenting exchange rates. Finally, the flow path of the shuttle exchange catheter simplifies the delivery catheter design, 13, removing the need for a central lumen, and therefore allowing more hollow fibers to be potted in the proximal and distal manifolds.

Figure 20:
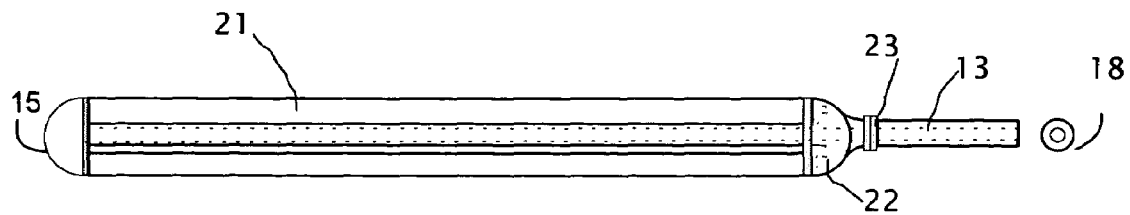
FIG. 20 shows a continuous flow microturbine exchange catheter.
Figure 20A:
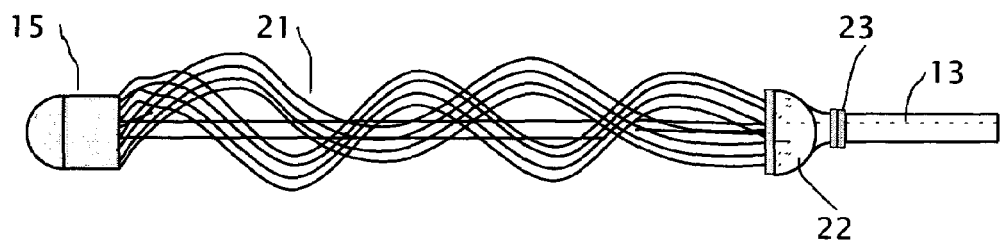
FIG. 20A shows a continuous flow microturbine exchange catheter with a helical hollow fiber or tube configuration FIG. 21 a three dimensional drawing of a section near the proximal manifold of the microturbine exchange catheter.
Figure 21:
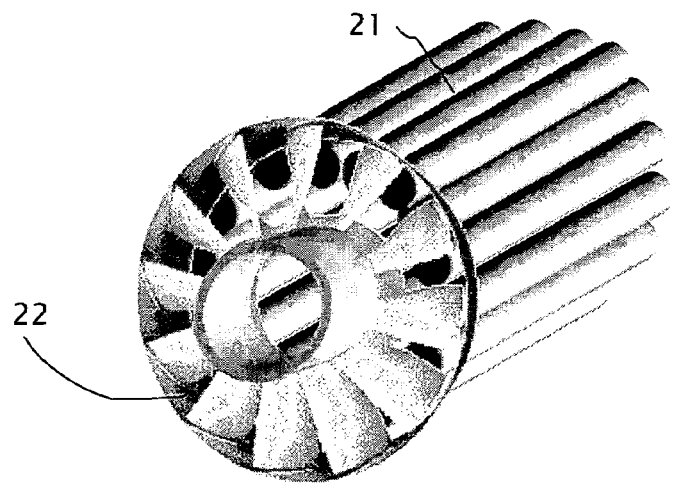
Figure 22:
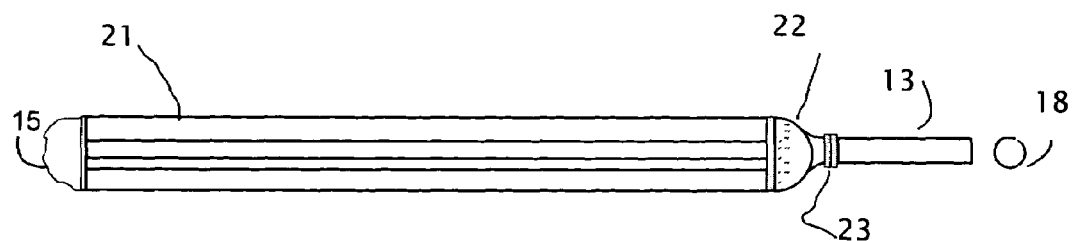
FIG. 22 shows a shuttle flow microturbine exchange catheter.

FIG. 20 shows another embodiment the employs rotational energy to create boundary layer disturbances. This exchange catheter uses microturbine, 22, and a sealed bearing, 23, to spin the fiber bundle and actively mix fluid around the fibers. The turbine is made of a stiff durable material, like stainless steel, carefully machined to an outer most diameter ranging from 2 to 5 mm. Sealed bearings to ensure ease of rotation with no blood infiltration. Like typical turbines the hydraulic energy, provided by the working fluid drive system (FIG. 5) of the coolant forces the turbine to spin. Combining the natural axial motion of the body fluid with the rotational motion of the tube bundle, 21, significant boundary disruption is achieved. FIG. 21 shows a three dimensional view of the microturbine exchange catheter. To address pressure drop issues that can result with this embodiment, the tube bundle 21, may take the shape of a helix creating (FIG. 20A) again a twisting motion that will motivate flow in the axial direction. To add an additional radial motion active mixing component this embodiment may also be used with compliant tubing and a shuttle working fluid drive system, FIG. 22. Like the embodiment described in FIG. 19, this embodiment also uses a distal collection balloon, 20.

Figure 23:
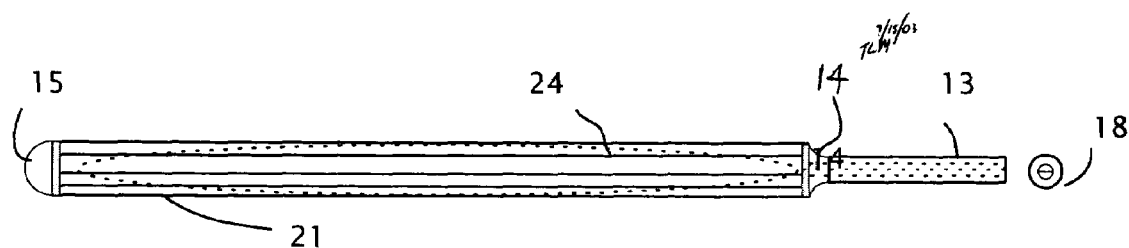
FIG. 23 shows an internal balloon exchange catheter.
Figure 24:
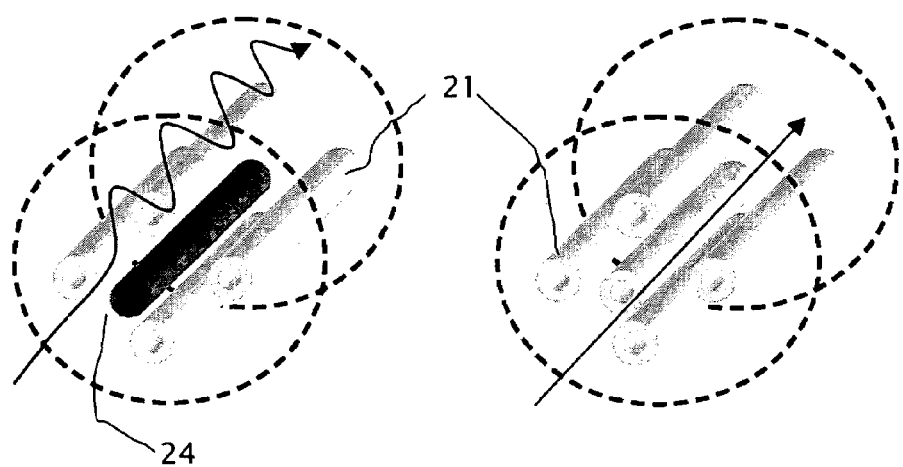
FIG. 24 shows the affect of balloon pulsation on a fluid particle pathline.
Figure 25:
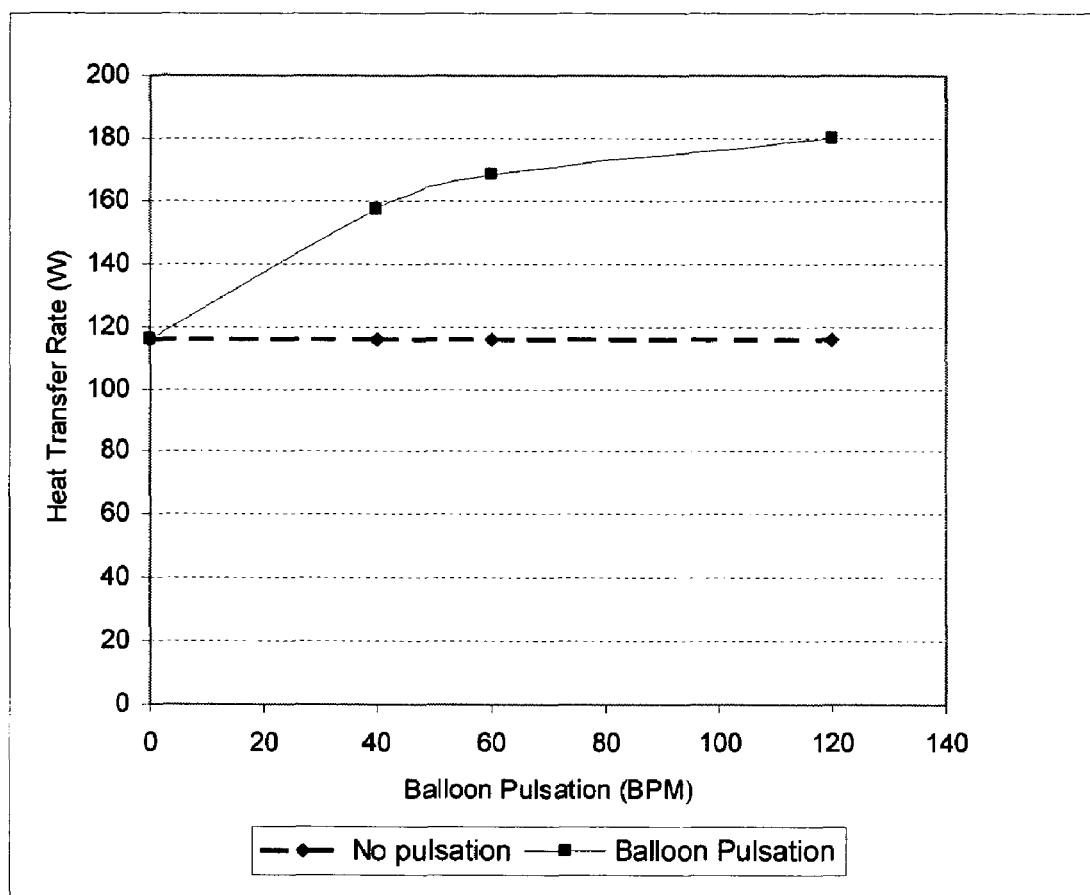
FIG. 25 show the affect of balloon pulsation on heat transfer rates.

FIG. 23 shows yet another embodiment where tubes or hollow fibers, 21 surround a pulsating balloon, 24. In this embodiment the balloon pulsation provides the active mixing necessary to augment exchange rates. Like previous embodiments the fibers or tubes carry the working fluid from the distal manifold, 15, to the proximal manifold and back to the working fluid drive system (FIG. 5). In this embodiment the balloon pulsation system, 12, creates radial motion disrupting adjacent boundary layers and lengthening the fluid pathline through the fiber or tube bundle, (FIG. 24). Typical pulsation rates range from 60 to 300 beats per minute. The influence of balloon pulsation is shown in FIG. 25, where a 50% increase in heat transfer is achieved at 120 beat per minute. Typical volumes for this internal active mixing balloon range from 0.2 ml to 10 ml.

Common additional properties to all embodiments are two characteristics not yet discussed: porous heat exchange surfaces and distal manifold design options.

First porous surfaces are surfaces having holes that are measured in fractions of a micrometer. Both balloons and hollow fibers may be made porous. These balloons and fibers can be purchased from Celgard Inc. Charlotte, N.C. and Advanced Polymers Inc. Salem, N.H. These pores enable simultaneous heat and mass transfer. In terms of mass transfer, alterations in blood gases or drug levels are possible with porous heat exchange surfaces. For example it has been shown that partial pressure increases of carbon dioxide may cause significant increases in blood perfusion to the brain (Reference: Cardiovascular Physiology, W. Milnor, Pg. 397, 1990). Under normal blood pressure conditions, an increase in carbon dioxide partial pressure from 40 mmHg to 60 mmHg causes a 40% increase in cerebral blood perfusion. The body responds to increases in carbon dioxide partial pressure with vasodilatation, reducing cerebral vascular resistance and increasing perfusion to the brain. In terms of blood oxygen content it has be shown that increases in blood oxygen partial pressure may help patients recover more successfully from head injury (Reference, Results of a prospective randomized trail for treatment of severely brain-injured patients with hyperbaric oxygen, G. Rockswold, Journal of Neurosurgery, Vol. 76, Pg. 929–934, 1992). In summary, porous heat exchange surfaces enable blood composition modifications to go beyond the thermal arena.

Figure 26:
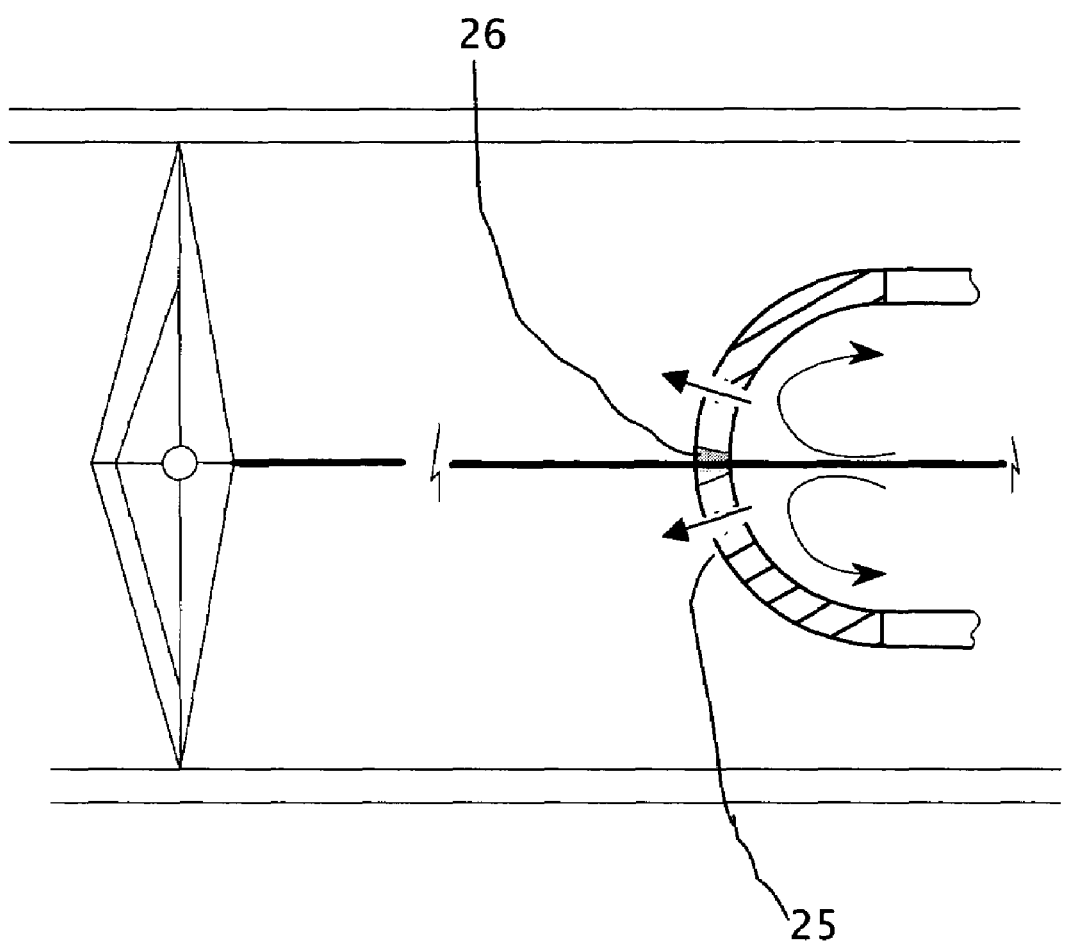
FIG. 26 show the distal manifold orifices for working fluid infusion.

Second, the distal manifold design may be altered to allow infusion of the working fluid and interconnection with distal protection filters (FIG. 26). Since flow through an orifice is dependent upon the pressure differential between the working fluid and the surrounding body fluid, the rate of infusion may be altered easily with the working fluid drive system. Furthermore, since the heat transfer resistance is dominated by the blood side convective term, there is a wide range of working fluid flow rates over which the impact of working flow rates changes has little or no effect on overall heat transfer. The orifice is designed to allow for elevated levels of infusion at the start of cooling and then reduced levels as the target temperature is reached, allowing heat exchange surface temperatures to maintain the target temperature. This distal manifold design creates a hybrid system, using both infusion techniques for rapid cooling and heat exchange techniques to maintain target temperatures. The distal protection interconnection allows the embodiments to benefit in two ways. First the distal protection filter helps align the orientation of the exchange catheter to ensure the exchange surfaces are fully utilized and in intimate contact with the body fluid. Second, the distal protection filter helps capture harmful emboli that may result from insertion and or operation.

An Clinical Application Example

The practice of the invention is shown in the following non-limiting example, Accordingly, the details of the procedure described below will change depending upon the application.

For this example we assume an ischemic stroke patient and we assume that there is a need to transfer heat and well as mass. There are two likely arterial locations for placement of the active mixing exchange catheters (FIGS. 10 through 23) in the common carotid artery or near the aortic arch. The exchange catheter selected for use is sized based on an ultrasound or magnetic resonance imaging (MRI) of the vessel size. Also, peak blood flow velocities are measured to ascertain blockages or vessel irregularities using similar ultrasound or magnetic resonance imaging techniques. Similar techniques are also used to identify particular brain regions affected by the stroke.

Using a standard angiography suite equipped with fluoroscopy, a guide catheter is placed in the desired common carotid artery. An appropriately sized exchange catheter is then filled with a perfluorocarbon emulsion. This size will typically range from 2–6 mm in diameter and 3–9 cm in length. The exchange catheter is then placed into the carotid artery via the guide catheter or over a guidewire and its placement is confirmed with fluoroscopy. Upstream of this placement a stint and or distal protection filter may be used to prevent further neurological complications from emboli or vessel wall movement. A stint may also be used to enable a larger cross sectional area for blood flow passage.

While the exchange catheter is being inserted, the primary working fluid circulation system and secondary conditioning fluid circulation system are readied for use. In this application the primary working fluid is a perfluorocarbon emulsion. The secondary circulation system has two components: a liquid system (saline or other coolant) to adjust primary working fluid temperature and a gas system (oxygen, carbon dioxide, nitrogen, etc.) to adjust the primary working fluid dissolved gas or therapeutic drug concentration. A hollow fiber device like a blood oxygenator may be used to adjust these parameters.

Assuming the exchange catheter has been placed in the common carotid artery of the ischemic stroke patient, cooling, gas delivery, and or drug delivery is begun by making the final connection between the exchange catheter and the working fluid drive system, FIG. 5. Also, drug or gas removal may also be conducted. Once connected, primary working fluid circulation is begun without pressure pulsation. The initiation of the circulation process carries cool oxygenated perfluorocarbon emulsion to and from the hollow fibers or tube of the preferred embodiment, FIG. 10. If system values for temperatures, pressures, and concentrations appear normal, a pressure pulsation rate of 30 beats per minute is begun. There are several ways to the adjust the rate of cooling, blood gas, and drug delivery: 1) the primary working fluid circulation rate can be changed (adjusting the internal heat and mass transfer coefficients), 2) the secondary conditioning fluid may be altered to change the primary working fluid inlet set points for temperature and concentration (adjusting the driving potentials for heat and mass transfer) and 3) the active mixing parameters can be altered (adjusting the dominant external or blood-side transfer coefficients). Typical operating conditions for the working fluid entering the exchange catheter may be 3–5 degrees Celsius and an inlet concentration of 50% oxygen by volume for the perfluorocarbon emulsion. The working fluid flow ranges from 100 to 300 ml/min depending on device size. The working fluid flow rate is chosen to minimize the internal convective heat transfer resistance at the lowest possible delivery pressure. Typical delivery pressures for the working fluid are 100 to 350 mmHg.

Throughout this and other clinical applications, the circulation or drive system described in FIG. 5 continues to monitor pressure, temperature, and concentrations. An algorithm inside the control system, FIG. 5, 11, ensures safe usage by triggering alarms if irregular conditions (in terms of pressure, temperature, or concentrations) are recorded. After a period time determined from clinical experience, the exchange catheter is removed and the patient is reevaluated. Typical cooling capacities range from 30 to 300 watts.

We claim:

1. A heat transfer device comprising:
   a multi-lumen catheter including a working fluid transfer pathway;
   a first manifold for connecting the multi-lumen catheter to a return pathway;
   a heterogeneous and compliant heat exchange portion connected to said first manifold, the heat exchange portion having a plurality of dynamic surface regions that provide internal and external boundary layer disruption;
   a second manifold connected to the heat exchange portion that distributes the working fluid through the heat exchange portion; and
   a high frequency working fluid pressure oscillator adapted to create surface dynamics in the heat exchange portion.

2. The heat transfer device of claim 1 wherein the heat exchange portion provides for substantially augmented heat exchange rates resulting from the fluid-device interaction of the plurality of dynamic surface regions.

3. The heat transfer device of claim 1, wherein said heterogeneous compliant heat exchange surface comprises segments of high and low compliance located adjacent to one another.

4. The heat transfer device in claim 1, wherein said heterogeneous compliant heat exchange surface comprises a plurality of individual heat exchange surfaces, each having higher compliant segments to disrupt fluid boundary layers and interconnected via the said working fluid manifolds.

5. The heat transfer device of claim 4 wherein the plurality of individual heat exchange surfaces comprises gas-permeable membranes having pores ranging from 0.01 to 0.05 micrometers.

6. The heat transfer device of claim 1, wherein said compliant heat exchange surface has individual segments of higher compliant material that move radially towards and away from the longitudinal axis of the heat transfer device.

7. The heat transfer device of claim 6 wherein the higher compliant segments are dynamic and travel towards and away from the longitudinal axis of the heat transfer device in the normal direction at a predetermined frequency.

8. The heat transfer device of claim 7 wherein the frequency is in the range of 1–20 Hz.

9. The heat transfer device of claim 6 wherein the higher compliant segments travel radial distances during each cycle of motion from a fully expanded position to a fully contracted position.

10. The heat transfer device of claim 9 wherein the radial distance is between 0.1 to 1 times the radius of the multi-lumen catheter radius.

11. The heat transfer device of claim 9 wherein the radial distance depends upon the lumen in which said heat transfer device is used.

12. The heat transfer device of claim 6 wherein when the higher compliant segments are in a fully expanded position have a shape that provides for boundary layer disruption and external fluid flow.

13. The heat transfer device of claim 12 wherein the higher compliant segments comprise radial rings.

14. The heat transfer device of claim 12 wherein the higher compliant segments comprise longitudinal protrusions.

15. The heat transfer device of claim 12 wherein the higher compliant segments comprise individual protrusions.

16. The heat transfer device of claim 12 wherein the higher compliant segments comprise helical protrusions.

17. The heat transfer device of claim 6 wherein the higher compliant segments expand and contract as a result of working fluid pressure oscillations at a predetermined frequency.

18. The heat transfer device of claim 17 wherein the working fluid pressure oscillations are created by substantially occluding the working fluid flow exiting the heat transfer device.

19. A heat transfer device comprising:
   a single lumen catheter including a working fluid pathway;

a compliant connective element connecting the single lumen catheter to a first manifold, the first manifold connecting said compliant connective element to a compliant heat exchange surface;

wherein during operation of the heat transfer device, the compliant heat exchange surface moves normal to and tangential to the longitudinal axis of the heat transfer device; and a second manifold connected to said compliant heat exchange surface adapted to collect working fluid that exits the compliant heat exchange surface; and a delivery device adapted to deliver working fluid to the inflatable distal manifold and remove working fluid from the inflatable distal manifold, thereby creating heat exchange surface dynamics.

20. The heat transfer device of claim 19 whereby the heat exchange process is augmented by minimizing fluid flow obstruction as a result of said single lumen structure, and by creating said heat exchange surface motion.

21. The heat transfer device of claim 19 wherein the second manifold is inflatable.

22. The device of claim 19, wherein said compliant heat exchange surface comprises a plurality of compliant tubes.

23. The device of claim 19, wherein the compliant tubes move inline with the longitudinal axis and normal to the longitudinal axis as said control system delivers and removes predetermined working fluid volume and to and from said inflatable distal balloon.

24. The device of claim 19, wherein the compliant connective element expands and contracts as said control system delivers and removes working fluid to and from said inflatable distal balloon.

25. A device for enabling a heat exchange process comprising:

a multi-lumen catheter for providing a working fluid pathway;

a proximal manifold for connecting said multi-lumen catheter, distributing the working fluid, and driving rotary motion of a compliant heat exchange surface;

a compliant heat exchange surface that spins about the longitudinal axis of the heat transfer device;

a distal manifold connected to said heat exchange surface adapted to collect the working fluid inside the said heat exchange surface; and a control system adapted to circulate the working fluid and drive the rotary motion of the proximal manifold;

whereby the heat exchange process is augmented by creating a circumferential heat exchange surface motion.

26. The device of claim 25 wherein the circumferential heat exchange surface motion reduces heat transfer resistance and promotes external fluid flow.

27. The device of claim 25, wherein said proximal manifold uses sealed bearings to ensure proper rotation with minimal blood infiltration.

28. The device of claim 25 further comprising an inflatable distal manifold.

29. The device of claim 25 further comprising a distal manifold that has a pressure dependent orifice that meters working fluid infusion as a function of working fluid internal pressure.

30. A method of altering organ temperature comprising:

inserting a guide wire and guide catheter into a patient;

inserting a distal protection filter along the guide catheter;

inserting a heat transfer device along a shaft of the distal protection filter;

locating the heat transfer device upstream of organ of interest;

positioning said heat transfer device concentric within an artery leading to the organ of interest;

circulating a gas soluble working fluid through said heat transfer device;

infusing said working fluid into external fluid to deliver rapid cooling in stage one of organ temperature alteration;

monitoring said infusion by applying mass balance about said working fluid and controlling internal working fluid pressure; and reducing or eliminating infusion of said working fluid to maintain organ temperature in stage two of organ temperature alteration.

* * * * *